(12) United States Patent
Hsiao et al.

(10) Patent No.: US 10,138,215 B2
(45) Date of Patent: Nov. 27, 2018

(54) PROCESS FOR PREPARING ATALUREN AND ITS INTERMEDIATES

(71) Applicant: ScinoPharm Taiwan, Ltd., Tainan (TW)

(72) Inventors: Tsung-Yu Hsiao, Tainan (TW); Yu-Hui Huang, Tainan (TW); Wei-Yu Chen, Tainan (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/626,325

(22) Filed: Jun. 19, 2017

(65) Prior Publication Data

US 2017/0362192 A1 Dec. 21, 2017

Related U.S. Application Data

(60) Provisional application No. 62/352,366, filed on Jun. 20, 2016.

(51) Int. Cl.
| | |
|---|---|
| C07D 271/06 | (2006.01) |
| C07C 63/06 | (2006.01) |
| C07C 25/125 | (2006.01) |
| C07C 249/04 | (2006.01) |
| C07C 251/32 | (2006.01) |

(52) U.S. Cl.
CPC .......... C07D 271/06 (2013.01); C07C 25/125 (2013.01); C07C 63/06 (2013.01); C07C 249/04 (2013.01); C07C 251/32 (2013.01)

(58) Field of Classification Search
CPC .................................................. C07D 271/06
See application file for complete search history.

(56) References Cited

U.S. PATENT DOCUMENTS

| | | | |
|---|---|---|---|
| 7,419,991 B2 * | 9/2008 | Karp ................... | A61K 31/4245 514/361 |
| 7,678,922 B2 | 3/2010 | Almstead et al. | |
| 8,367,841 B2 | 2/2013 | Almstead et al. | |
| 2004/0204461 A1 | 10/2004 | Karp et al. | |

FOREIGN PATENT DOCUMENTS

| | | |
|---|---|---|
| CN | 105461650 A | 10/2004 |
| WO | 2006110483 A1 | 4/2009 |
| WO | 2009043889 A2 | 4/2009 |
| WO | 2016073545 A1 | 5/2016 |

OTHER PUBLICATIONS

International Search Report dated Sep. 19, 2017 for PCT Application No. PCT/SG2017/050310, filed Jun. 20, 2017, 5 pages.
Written Opinion dated Sep. 19, 2017 for PCT Application No. PCT/SG2017/050310, filed Jun. 20, 2017, 7 pages.

* cited by examiner

*Primary Examiner* — Laura L Stockton
(74) *Attorney, Agent, or Firm* — Mintz, Levin, Cohn, Ferris, Glovsky and Popeo, P.C.

(57) ABSTRACT

The present invention provides processes for the preparation of ataluren. Intermediates for preparing ataluren are also provided.

24 Claims, 3 Drawing Sheets

PROCESS FOR PREPARING ATALUREN AND ITS INTERMEDIATES

CROSS-REFERENCES TO RELATED APPLICATIONS

This application claims the benefit of priority to U.S. Provisional Application Ser. No. 62/352,366, filed Jun. 20, 2016, the contents of which are incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Ataluren (formerly known as PTC124), which is chemically named as 3-[5-(2-fluorophenyl)-1,2,4-oxadiazol-3-yl] benzoic acid, is an orally administered small-molecule compound for the treatment of patients with genetic disorders (e.g., Duchenne muscular dystrophy (DMD) and cystic fibrosis) caused due to a nonsense mutation. Ataluren is discovered and designed by PTC Therapeutics, Inc. and is sold under the trade name Translarna™ in the European Union. Translarna™ is the first treatment approved for the underlying cause of DMD. The European Medicines Agency (EMA) has designated ataluren as an orphan medicinal product.

Publications related to ataluren reveal several synthetic approaches which have mostly been disclosed by PTC Therapeutics, Inc. The synthetic approaches disclosed in the prior art are described below.

WO 2006/110483 A1 discloses methods for preparing ataluren. As specifically illustrated in FIG. 1, 3-cyanobenzoic acid methyl ester compound 1 was reacted with hydroxylamine to form oxime compound 2 as white powder. The oxime compound 2 was contacted with 2-fluorobenzoyl chloride to form compound 3 under basic condition. Then put compound 3 into toluene at high temperature to complete condensation and form oxadiazole compound 4. The compound 4 was subjected to hydrolysis conditions (aqueous NaOH) and then ataluren formed as white powder. The overall yield from compound 1 to ataluren was about 73%.

Another approach is a one-pot process disclosed in U.S. Pat. Nos. 7,678,922 B2 and 8,367,841 B2 (see FIG. 2). The synthetic route also started from 3-cyanobenzoic acid methyl ester compound 1 without the isolation of compounds 2, 3 and 4 to afford ataluren. Tert-Butanol was used as the main solvent system through this route, even in the final hydrolysis step. The overall yield from compound 1 to ataluren was about 67-69%.

Still another one-pot process of ataluren disclosed in U.S. Pat. Nos. 7,678,922 B2 and 8,367,841 B2 is started from 3-cyanobenzoic acid, compound 5, without the isolation of compounds 6 and 7 (see FIG. 3). Tert-Butanol was also used as the main solvent system for this approach. The overall isolation yield of ataluren was about 76%.

Although numerous approaches for preparing ataluren have been disclosed as discussed above, there is still an unmet need for a mild, cleaner and easier process for industrial preparation of ataluren. The present processes disclosed herein address this need and other needs.

BRIEF SUMMARY OF THE INVENTION

In one aspect, the present invention provides a process for the preparation of ataluren

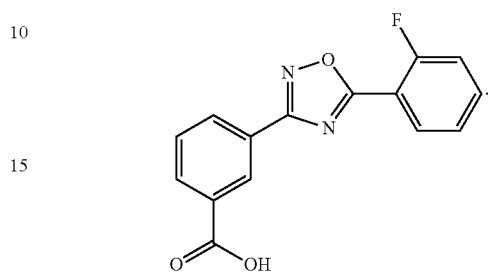

The process includes:
a) contacting a compound of formula I

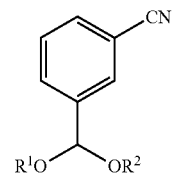

with hydroxylamine to provide a compound of formula II

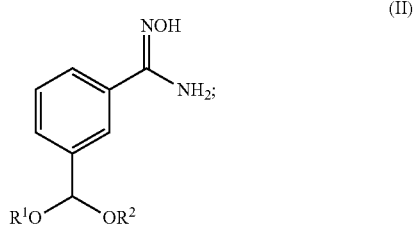

and
b) converting the compound of formula II to ataluren; wherein $R^1$ and $R^2$ are independently selected from the group consisting of $C_1$-$C_6$ alkyl and $C_1$-$C_6$ acyl; or $R^1$ and $R^2$ are taken together to form an optionally substituted 5-7 member cyclic acetal.

In a second aspect, the present invention provides a compound of formula II

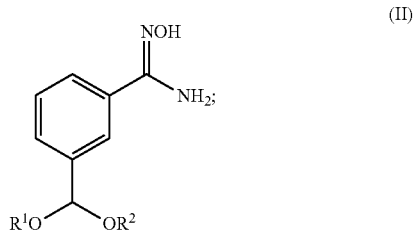

wherein $R^1$ and $R^2$ are independently selected from the group consisting of $C_1$-$C_6$ alkyl and $C_1$-$C_6$ acyl; or $R^1$ and $R^2$ are taken together to form an optionally substituted 5-7 member cyclic acetal.

In a third aspect, the present invention provides a process for the preparation of ataluren;
The process includes:
a) contacting a compound of formula VI

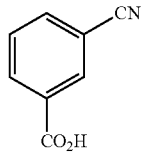
(VI)

with hydroxylamine to provide a compound of formula VII

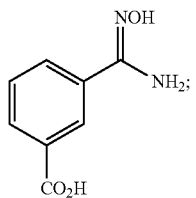
(VII)

b) contacting the compound of formula VII with the compound of formula III

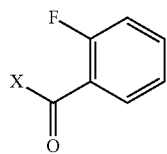
(III)

to provide a compound of formula VIII

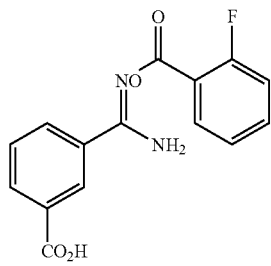
(VIII)

in a two-phase basic condition having a basic aqueous solution and an organic solvent; and
c) converting the compound of formula VIII to ataluren; wherein X is a leaving group.

DETAILED DESCRIPTION OF THE INVENTION

I. General

Figure 1:
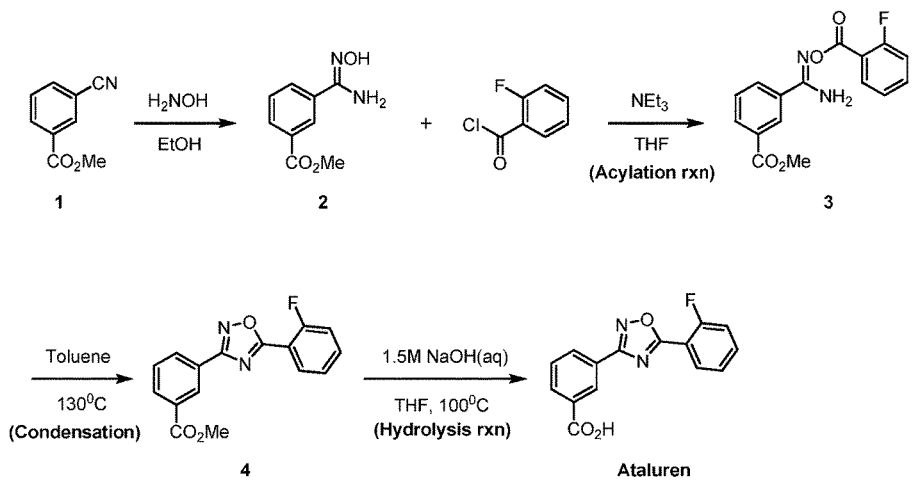
FIG. 1 shows the synthetic route for ataluren disclosed in WO 2006/110483 A1.
Figure 2:
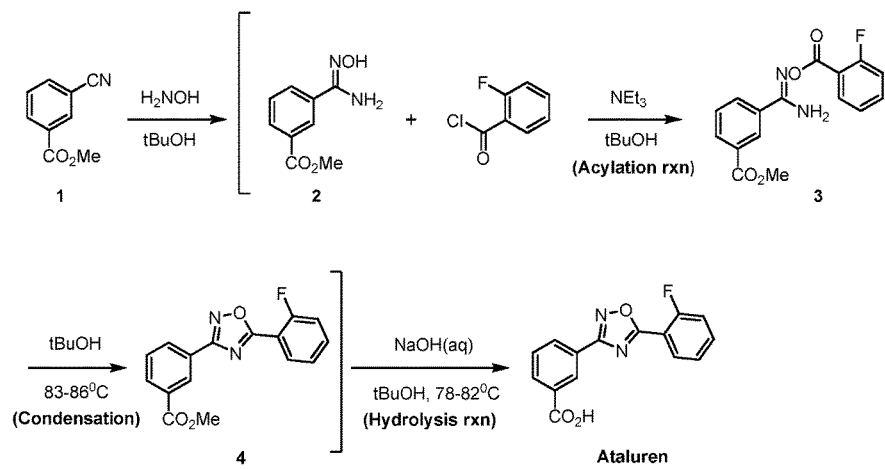
FIG. 2 shows the synthetic route for ataluren disclosed in U.S. Pat. Nos. 7,678,922 B2 and 8,367,841 B2 (one-pot reaction started from 3-cyanobenzoic methyl ester).
Figure 3:
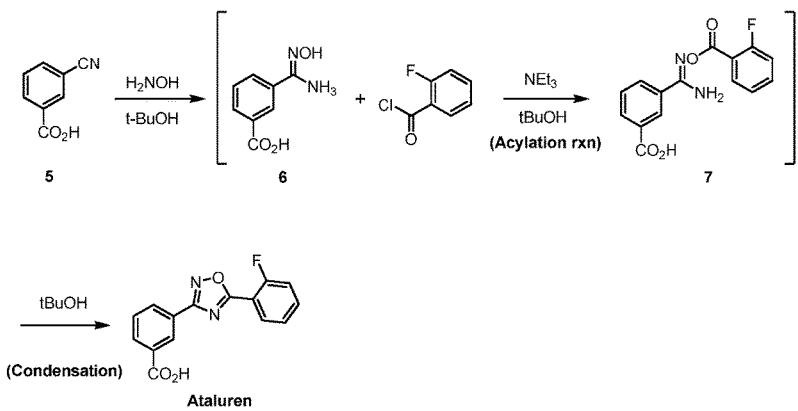
FIG. 3 shows the synthetic route for ataluren disclosed in U.S. Pat. Nos. 7,678,922 B2 and 8,367,841 B2 (one-pot reaction started from 3-cyanobenzoic acid).

The present invention provides novel processes for preparation of ataluren. The aldehyde acetal compound of formula I utilized in the present invention provides electron-donating group that can accelerate reaction rates of oxime formation and acylation, and both two reactions can be conducted at lower reaction temperature. The present invention also provides acylation in two-phase solvent system, which makes the isolation of the compound of formula IV much cleaner and easier. A person of skill in the art will recognize that in addition to the novel processes described herein, the present application also provides novel intermediate compounds.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "acyl" refers to an alkyl radical as described above, wherein the carbon atom attached to the remainder of a molecule is substituted with an oxo group so as to form a C=O bond. Acyl substituents may contain number designators indicating the number of carbon atoms in the substituent (i.e. $C_1$-$C_6$ means one to six carbon atoms), although such designators may be omitted. Examples of acyl groups include, but are not limited to, acetyl, propionyl, butyryl, and the like.

As used herein, the term "leaving group" refers to a moiety that can be displaced by a nucleophile in a substitution reaction. Examples of useful leaving groups useful include, but are not limited to, halogens (i.e., I, Br, Cl, and F), sulfonates (such as p-toluenesulfonate, methansulfonate, and the like), carboxylates (such as acetic acid, ethanoic acid, propionic acid, trifluoroacetic acid, and the like), alkoxides, phosphates, phenoxides, O-succinimides (OSu), or O-phtalimides.

As used herein, the term "one-pot reaction" refers to a reaction in which a starting material undergoes at least two sequential chemical transformations in a single reaction vessel. In general, compounds formed as intermediates in the sequence are not isolated from a one-pot reaction mixture. Reagents necessary to affect the transformation sequence may be added together at the beginning of the sequence, or they may be added one after another as the sequence progresses.

As used herein, the term "protecting reagent" refers to a reagent capable of reacting with a functional moiety to form a protecting group that renders the functional moiety unreactive. The protecting group is also removable so as to restore the functional moiety to its original state. A protecting reagent can be an "aldehyde protecting reagent" wherein the protected functional moiety is an aldehyde. Such reagents are capable of reacting with aldehydes to form protecting groups including acetals, cyclic acetals, monothioacetals, dithioacetals, and hydrazones. Various protecting groups and protecting reagents, including aldehyde protecting reagents, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

III. Embodiments of the Invention

In one aspect, the present invention provides a process for the preparation of ataluren:

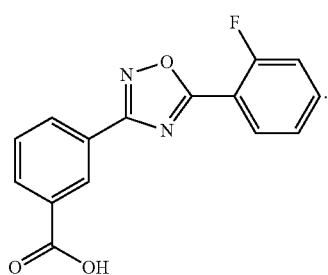

The process includes:
a) contacting a compound of formula I

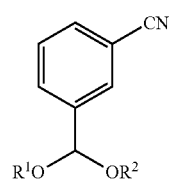

(I)

with hydroxylamine to provide a compound of formula II

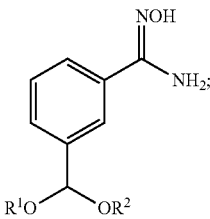

(II)

and
b) converting the compound of formula II to provide ataluren;
wherein $R^1$ and $R^2$ are independently selected from the group consisting of $C_1$-$C_6$ alkyl and $C_1$-$C_6$ acyl; or
$R^1$ and $R^2$ are taken together to form an optionally substituted 5-7 member cyclic acetal.

In the present invention, the compound of formula I (i.e., 3-cyanobenzaldehyde acetal) is employed as the main starting material. An advantage of the present process is the inclusion of an electron-donating group in the meta-position of a cyano substituted benzene. Compared to 3-cyanobenzoic acid methyl ester (an electron-withdrawing group, as used in WO 2006/110483 A1), the present process increases the reaction rates of oxime formation (the compound of formula II) and acylation (the compound of formula IV), such that both reactions can be achieved under mild conditions (e.g., lower reaction temperature).

The rate of oxime formation (i.e. converting a compound of formula I to a compound of formula II) is determined, in part, by the temperature of the reaction and the overall reaction time. In some embodiments, the temperature of the reaction is from 40-60° C. or 45-55° C. In some embodiments, the temperature of the reaction is about 50° C. In some embodiments, the reaction is incubated for 1-4 hours. In some embodiments, the reaction is incubated about 2.5 hours.

The conversion of step a) (i.e. converting a compound of formula I to a compound of formula II) can be performed in various solvents. For example, in some embodiments, the solvent is a protic solvent. In some embodiments, the solvent is a mixture of solvents including a protic solvent. In some embodiments, the protic solvent is an alcohol solvent. In some embodiments, the alcohol solvent is selected from the group consisting of methanol, ethanol, propanol, butanol, or a combination thereof.

The yield of the reaction is dependent on both the reaction temperature and the incubation time. In some embodiments, the yield of the reaction is from 80-99% or 85-95%. In some embodiments, the yield of the reaction is about 88%.

In some embodiments, step b) further comprises:
i) contacting the compound of formula II with a compound of formula III

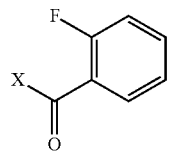

(III)

to provide a compound of formula IV

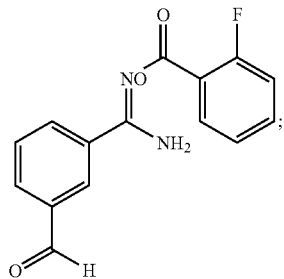

(IV)

ii) converting the compound of formula IV to provide a compound of formula V

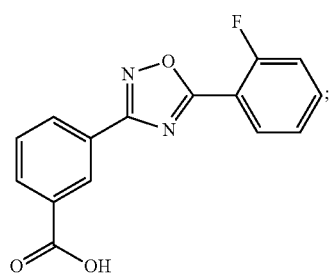 [SMILES: O=C(O)c1cccc(-c2noc(-c3ccccc3F)n2)c1]

(V)

and iii) oxidizing the compound of formula V to ataluren; wherein X is a leaving group.

Figure 4:
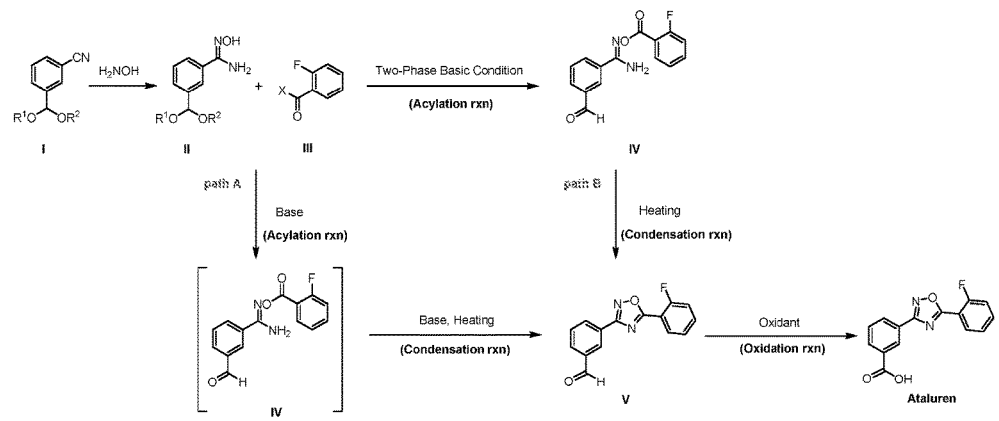
FIG. 4 shows the synthetic route for ataluren described in the present application (Paths A and B).

In some embodiments, steps i) to ii) are conducted in a one-pot reaction (see FIG. 4, Path A). In some embodiments, the one-pot reaction is conducted in an organic solvent selected from the group consisting of pyridine, toluene, xylene and mixtures thereof. In some embodiments, the organic solvent is pyridine. The one-pot reaction can be conducted in an organic base selected from the group consisting of pyridine, trimethylamine (TEA), diisopropylethylamine (DIPEA) and mixtures thereof. In some embodiments, the organic base is pyridine. In some embodiments, the organic solvent and the organic base is a single chemical, thereby reducing the number of required reagents.

An advantage of the one pot reaction is that the de-protection of the acetal functional group found in formula II (de-acetalation) can be simultaneously achieved in the acylation step and/or the condensation step.

The one-pot reaction is initiated by contacting a compound of formula II with the compound of formula III. In some embodiments, the compound of formula II is added to the compound of formula III. In some embodiments, the compound of formula III is added to the compound of formula II. Any suitable rate of addition can be used. In some embodiments, one reagent is slowly added to the other reagent.

The contacting step can be performed at a variety of temperatures. In some embodiments, the one-pot reaction is cooled to between 0-10° C. for the contacting step. In other embodiments, the one-pot reaction is cooled to about 5° C.

After contacting the compound of formula II and the compound of formula III in the one-pot reaction, the temperature is generally raised to increase the rate of the condensation reaction. In some embodiments, the mixture is headed to between 80-110° C. In some embodiments, the mixture is heated to about 92-98° C.

The amount of time the one-pot reaction is incubated at the elevated temperature will vary depending on the incubation temperature of the reaction. In some embodiments, the incubation time of the one-pot reaction is between 15-25 hours. In some embodiments, the incubation time is about 20 hours.

The one-pot reaction efficiently produces a compound of formula V. The overall yield for the conversion of a compound of formula II to the compound of formula V in (see FIG. 4, Path A) is generally at least 75%. In some embodiments, the yield is from 75-95%, 77-87%, or 80-84%. In some embodiments, the yield is about 82%.

In some embodiments, the acylation of step i) is carried out in a two-phase solvent system having a basic aqueous solution and an organic solvent (see FIG. 4, Path B). In some embodiments, the basic aqueous solution is $NaHCO_{3\ (aq)}$, $Na_2CO_{3\ (aq)}$, $K_2CO_{3\ (aq)}$ or mixtures thereof. In other embodiments, the basic aqueous solution is $NaHCO_{3\ (aq)}$. In some embodiments, the organic solvent is ethyl acetate, toluene, dichlormethane (DCM), 2-methyltetrahydrofuran (2-MeTHF) and mixtures thereof. In some embodiments, the organic solvent is ethyl acetate.

In the acylation reaction of path B, the compound of formula II is dissolved in the basic aqueous solution and the compound of formula III is dissolved in the organic solvent. The two phases are then contacted to initiate the reaction. In some embodiments, the solution containing a compound of formula II is added to the solution containing a compound of formula III. In some embodiments, the solution containing a compound of formula III is added to the solution containing a compound of formula II. Any suitable rate of addition can be used. In some embodiments, one reagent is slowly added to the other reagent.

After completion of the acylation reaction in path B, the acylation product is de-acetalated. This may be completed using a variety of techniques known in the art. In some embodiments, a single extraction of the two phases solvent system is employed, where the aqueous layer is discarded and the organic layer is saved (the acylation product is in the organic layer). The saved organic layer is stirred at 20-30° C. for 1-5 hours to form a compound of formula IV. In some embodiments, the stirring is for about 3 hours. A person of skill in the art will appreciate that alternative work-up and de-acetalation steps/conditions may be employed without diverging from the scope of the present method.

The acylation and de-acetalation of path B produces robust yields of a compound of formula IV. In some embodiments, the yield of this transformation is generally at least 80%. In some embodiments, the yield of this transformation is from 80-95%, 85-95%, or 87-93%. In some embodiments, the yield of this transformation is about 90%.

The conversion of the compound of formula IV to a compound of formula V can be achieved using a number of different condensation reaction conditions. In some embodiments, a compound of formula IV is dissolved in organic solvent and heated for an amount of time to produce a compound of formula V. In some embodiments the organic solvent is selected from the group consisting of toluene, benzene, cyclohexane, ethyl acetate, dichlorormethane, and 2-methyl tetrahydrofuran. In some embodiments, the organic solvent is toluene. In some embodiments the temperature reaction mixture can range from 75-95° C. or 80-90° C. In some embodiments, the mixture is heated to about 85° C. The temperature chosen will affect the incubation time and/or yield of the reaction. In some embodiments, the reaction mixture is incubated for 15-20 hours. In some embodiments, the reaction mixture is incubated for about 20 hours.

The overall yield for the conversion of the compound of formula II to the compound of formula V in path B is generally at least 75% In some embodiments, the yield is from 75-95% or 80-90%. In some embodiments the yield is about 86%.

The conversion of V to ataluren can be conducted under a variety of oxidative conditions. In some embodiments, the oxidation of V includes the addition of an oxidant selected from the group consisting of chlorite, a transition metal catalyst, nickel peroxide, meta-chloroperoxybenzoic acid (m-CPBA), tert-butyl hydroperoxide (TBHP), potassium peroxomonosulfate (Oxone), and mixtures thereof. In some embodiments, the chlorite is selected from the group consisting of chlorous acid, magnesium chlorite, sodium chlorite, and potassium chlorite. In some embodiments, the oxidant is sodium chlorite.

The oxidation step can be conducted in a buffered solution. In some embodiments, the oxidation step is conducted with a chlorite that is buffered with an electrolyte selected from the group consisting of HCl/sodium citrate, citric acid/sodium citrate, acetic acid/sodium citrate, potassium dihydrogen phosphate, dipotassium phosphate/sodium dihydrogen phosphate, and disodium phosphate mixtures. In some embodiments the electrolyte is potassium dihydrogen phosphate.

A variety of aldehyde protecting reagents can be used in the methods of the present invention. Suitable reagents are capable of reacting with aldehydes to form protecting groups, including but not limited to acetals, monothioacetals, dithioacetals, and hydrazones. Such protecting groups can be removed to restore the aldehyde moiety. In some embodiments, the aldehyde protecting reagent is selected from the group consisting of trimethyl orthoformate (TMOF), triethylorthoformate, triethyl orthoacetate, trimethyl orthoacetate, acetic anhydride, ethylene glycol, and propylene glycol. In some embodiments, the aldehyde protecting reagent is trimethylorthoformate (TMOF). One of skill in the art will appreciate that still other aldehyde protecting reagents may be useful in the present invention.

In some embodiments, the invention provides a compound of formula II:

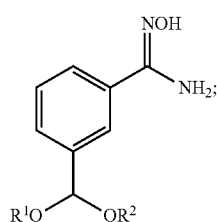

(II)

wherein $R^1$ and $R^2$ are independently selected from the group consisting of $C_1$-$C_6$ alkyl and $C_1$-$C_6$ acyl; or $R^1$ and $R^2$ are taken together to form an optionally substituted 5-7 member cyclic acetal.

In some embodiments, the compound of formula II is IIa

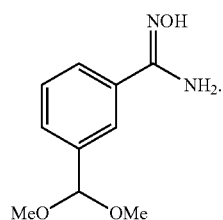

(IIa)

In a related aspect, the present invention provides a process for the preparation of a compound of structure VIII
a) contacting a compound of formula VI

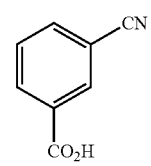

(VI)

with hydroxylamine to provide a compound of formula VII

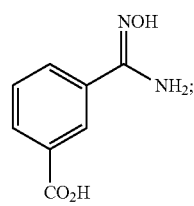

(VII)

b) contacting the compound of formula VII with the compound of formula III

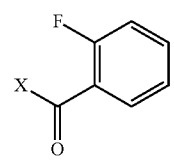

(III)

to provide a compound of formula VIII

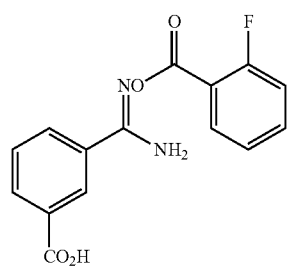

(VIII)

in a two-phase basic condition having a basic aqueous solution and an organic solvent; and c) converting the compound of formula VIII to provide ataluren;

wherein X is a leaving group

Figure 5:
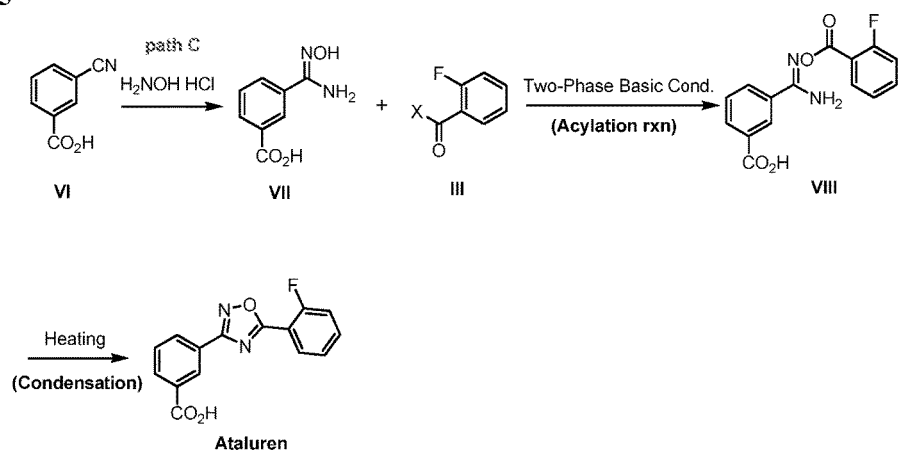
FIG. 5 shows another synthetic route for ataluren described in the present application (Path C).

As described above, the two-phase solvent system was also applied in benzoic acid system for acylation reaction (FIG. 5, Path C). In some embodiments embodiment, the basic aqueous solution is selected from the group consisting of NaHCO$_3$ $_{(aq)}$, Na$_2$CO$_3$ $_{(aq)}$ and K$_2$CO$_3$ $_{(aq)}$. In some embodiments, the basic aqueous solution is K$_2$CO$_3$ $_{(aq)}$. In some embodiments, the organic solvent is selected from the group consisting of ethyl acetate, toluene and mixtures thereof. In some embodiments, the organic solvent is toluene.

In the acylation reaction of path C, the compound of formula VII is dissolved in the basic aqueous solution and the compound of formula III is dissolved in the organic solvent. The two phases are contacted to initiate the reaction. In some embodiments, the solution containing a compound of formula VII is added to the solution containing a compound of formula III. In some embodiments, the solution containing a compound of formula III is added to the solution containing a compound of formula VII. Any suitable rate of addition can be used. In some embodiments, one reagent is slowly added to the other reagent.

As described in the process of present invention, the leaving group of the compound of formula III is selected from the group consisting of a halogen, an O-succinimide (i.e., N-Hydroxysuccinimide), an —O—R$^a$, a carboxylate, a phenoxide, and an anhydride; wherein R$^a$ is C$_1$-C$_6$ alkyl. In some embodiments, the leaving group of the compound of formula III is selected from the group consisting of a halogen, an O-succinimide (i.e., N-Hydroxysuccinimide), an —O—R$^a$, a carboxylate, and a phenoxide; wherein R$^a$ is C$_1$-C$_6$ alkyl. One of skill in the art will appreciate that still other leaving groups are useful in the present invention.

The acylation of path C produces robust yields of a compound of formula VIII. In some embodiments, the yield of this transformation is generally at least 80%. In some embodiments, the yield of this transformation is from 80-95%, 85-95%, or 87-93%. In some embodiments, the yield of this transformation is about 90%.

The next conversion in path C, converts a compound of formula VIII to ataluren. This can be achieved using the same condensation conditions as reported in U.S. Pat. No. 7,678,922 B2 and U.S. Pat. No. 8,367,841 B2 to give ataluren in about 88% yield.

The overall yield from the compound of formula VII to ataluren can range from 60-90%. In some embodiments, the yield is 75-85%. In some embodiments the yield is about 79%.

IV. Examples

The following examples are presented to describe the invention in further detail. However, the present invention is by no means restricted to the specific embodiments described herein.

Abbreviations used are those commonly used in the art. Exemplary abbreviations used include mL (milliliters), mmol (millimoles), equiv. (equivalents), DCM (dichloromethane), PPW (partially purified water), min (minutes), vol. (volume), hr (hour), NMT (no more than), NLT (not longer than).

Example 1

Synthesis of 3-(dimethoxymethyl)benzonitrile (Ia)

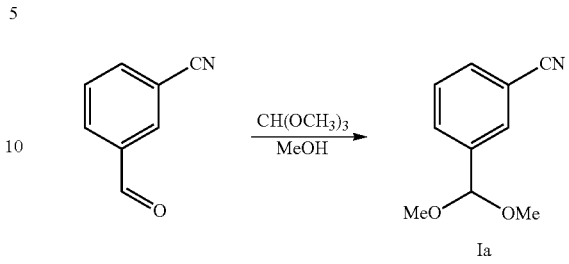

3-Cyanobenzaldehyde (5 g, 38.13 mmol, 1.0 equiv.) and MeOH (60 mL, 12 vol.) were added to a suitable reactor equipped with a stir bar and a thermometer at 20-30° C. and stirred for about 5 min. A solution of trimethyl orthoformate (25.08 mL, 6.0 equiv.) in MeOH (15 mL, 3 vol.) was added at this temperature for NLT 5 min. 32% HCl$_{(aq)}$ (1.125 mL, 0.3 equiv.) was slowly added to the mixture at 20-30° C. Then the reaction mixture was heated to 45° C. and stirred for NLT 3 hr. After reaction was completed as determined by TLC analysis, the mixture was cooled to NMT 20° C. Saturated Na$_2$CO$_3$ (aq) (1.0 mL, 0.2 vol.) was added at this temperature adjusting pH to about 6-7. Then the neutral solution was concentrated to dryness affording pale yellowish liquid. DCM (30 mL, 6 vol.) was added to dissolve the resulting liquid and PPW (20 mL, 4 vol.) was added to wash the DCM solution. After the mixture was stirred about 5 min, the stirring was stopped for about 1-2 min to affect phase separation. The separated organic portion was saved, and the separated aqueous portion was washed with another DCM (10 mL, 2 vol.). After the mixture was stirred about 5 min, the stirring was stopped for about 1-2 min to affect phase separation. The separated organic portion was saved, and the separated aqueous portion was discarded. The organic portions were combined and concentrated to dryness under reduced pressure at NMT 30° C. to give 3-(dimethoxymethyl)benzonitrile (Ia) as colorless to pale yellow liquid (6.68 g, 98.9% yield based on 3-cyanobenzaldehyde). $^1$H-NMR (400 MHz, CDCl$_3$) δ7.80 (m, 1H), 7.71 (m, 1H), 7.64 (dt, 1H), 7.50 (t, 1H), 5.43 (s, 1H), 3.34 (s, 1H).

Example 2

Synthesis of 3-(dimethoxymethyl)-N'-hydroxybenzimidamide (IIa)

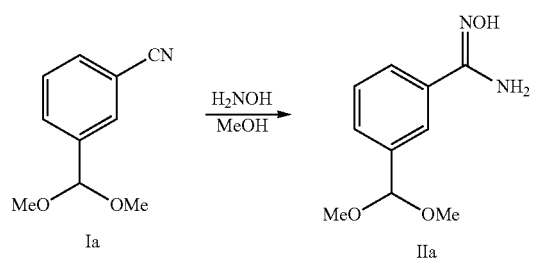

3-(dimethoxymethyl)benzonitrile (Ia) (6 g, 33.86 mmol, 1.0 equiv.) and MeOH (30 mL, 5 vol) were added to a suitable reactor equipped with a stir bar and a thermometer at 20-30° C. and stirred for about 5 min. An aqueous solution of hydroxylamine (50 wt % in water) (3.11 mL, 1.5 equiv.) was added at this temperature. Then the reaction mixture was heated to 50° C. and stirred for 2.5 hr. After the reaction was completed as determined by TLC analysis, the solution was cooled to ambient temperature. The mixture was diluted with DCM (60 mL, 10 vol) and washed with PPW (36 mL, 6 vol). The mixture was stirred at 20-30° C. for 5-10 min, and then the phases were allowed to separate and the organic and aqueous portions were respectively saved. The DCM portion was washed with PPW (48 mL, 8 vol) for twice. The aqueous portions were combined and washed with DCM (60 mL, 10 vol) for one time. After stirred at 20-30° C. for 5-10 min, the layers were separated and the aqueous portion was discarded. The organic portions were combined and concentrated to dryness under reduced pressure at NMT 30° C. to give 3-(dimethoxymethyl)-N'-hydroxybenzimidamide (IIa) as white solid (6.26 g, 88% yield based on Ia). $^1$H-NMR (400 MHz, CDCl$_3$) δ7.74 (m, 1H), 7.65 (dt, 1H), 7.54 (m, 1H), 7.43 (t, 1H), 5.44 (s, 1H), 4.94 (brs, 2H), 3.36 (s. 6H).

Example 3

Synthesis of N'-((2-fluorobenzoyl)oxy)-3-formyl-benzimidamide (IV)

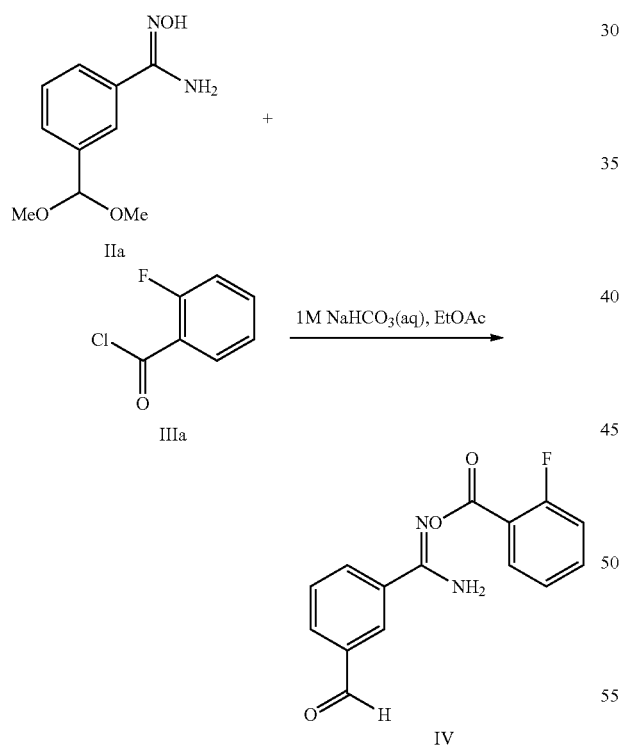

3-(dimethoxymethyl)-N'-hydroxybenzimidamide (IIa) (0.5 g, 2.38 mmol, 1.0 equiv.) and 1M aqueous solution of NaHCO$_3$ (4 mL, 8 vol) were added to a suitable reactor equipped with a stir bar and a thermometer at 20-30° C. and stirred for about 5 min. A solution of 2-fluorobenzoyl chloride (IIIa) (0.457 mL, 2 equiv.) in dry EtOAc (1 mL, 2 vol) was slowly added at this temperature. Dry EtOAc (1 mL, 2 vol) was added to rinse the reactor. Then the reaction mixture was stirred at 20-30° C. for 1 hr. After the reaction was completed as determined by TLC analysis, the phases were allowed to separate and EtOAc (5 mL, 10 vol) was added to rinse the reactor. The aqueous portion was discarded and EtOAc solution was stirred for 3 hr at this temperature. After transformation was completed as determined by TLC analysis, solution was washed with PPW (10 mL, 20 vol) for three times. The aqueous portions were discarded and the organic portion was concentrated to dryness under reduced pressure at NMT 30° C. to give crude N'-((2-fluorobenzoyl)oxy)-3-formylbenzimidamide (IV) as white solid (0.876 g, >100% yield). Crude N'-((2-fluorobenzoyl)oxy)-3-formylbenzimidamide (0.876 g, 3.06 mmol, 1.0 equiv.) and toluene (5 mL, 10 vol) were added to a suitable reactor equipped with a stir bar and a thermometer at 20-30° C. The reaction mixture was stirred at this temperature for 1 hr, followed by cooled to 0-10° C. (target 5° C.) and stirred for 2 hr. Then the mixture was filtered and the filtered cake was washed with pre-cooled toluene (1.5 mL, 3 vol) two times. The wet cake was suction dried at NMT 40° C. with N$_2$ purge for NLT 18 hr to give pure N'-((2-fluorobenzoyl)oxy)-3-formylbenzimidamide (IV) as white solid (0.589 g, 90% yield based on crude IV). $^1$H-NMR (400 MHz, D$_6$-DMSO) δ10.10 (s, 1H), 8.32 (t, 1H), 8.10 (m, 3H), 7.72 (m, 2H), 7.39 (m, 2H), 7.08 (brs, 2H).

Example 4

Synthesis of 3-[5-(2-fluorophenyl)-1,2,4-oxadiazol-3-yl]benzaldehyde (V)

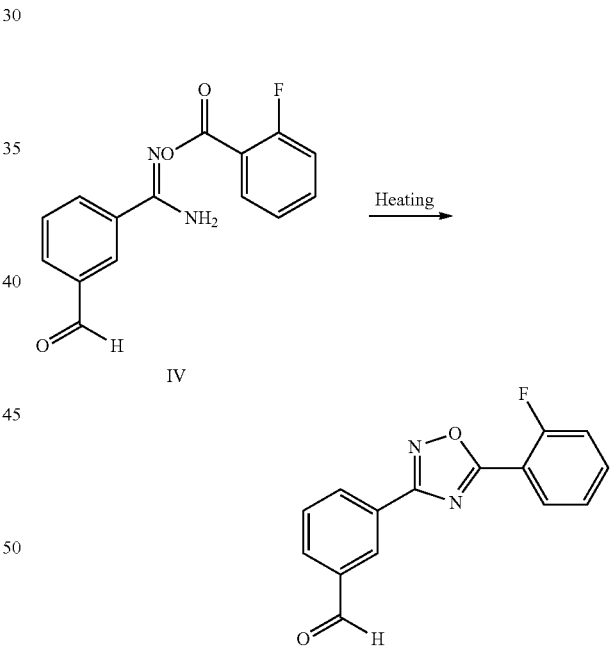

Pure N'-((2-fluorobenzoyl)oxy)-3-formylbenzimidamide (IV) (0.5 g, 1.75 mmol, 1.0 equiv.) and toluene (10 mL, 20 vol) were added to a suitable reactor equipped with a stir bar and a thermometer at 20-30° C. and stirred for about 5 min. The reaction mixture was heated to 85° C. and stirred for 18 hr. After the reaction was completed as determined by TLC analysis, the solution was cooled to 20-30° C. The mixture was diluted with EtOAc (3 mL, 6 vol) and washed with PPW (10 mL, 20 vol). After stirring for 5 min at 20-30° C., the phases were allowed to separate and the aqueous portion was discarded. The EtOAc portion was washed with another PPW (10 mL, 20 vol) for twice. The organic portion was concentrated to dryness under reduced pressure at NMT 30° C. to give crude 3-[5-(2-fluorophenyl)-1,2,4-oxadiazol-3-yl]benzaldehyde (V) as white solid (0.475 g, 95% yield). $^1$H-NMR (400 MHz, D$_6$-DMSO) δ10.17 (s, 1H), 8.61 (t, 1H), 8.42 (dt, 1H), 8.28 (td, 1H), 8.18 (dt, 1H), 7.84 (m, 2H), 7.57 (m, 2H).

Example 5

Synthesis of 3-[5-(2-fluorophenyl)-1,2,4-oxadiazol-3-yl]benzaldehyde (V)

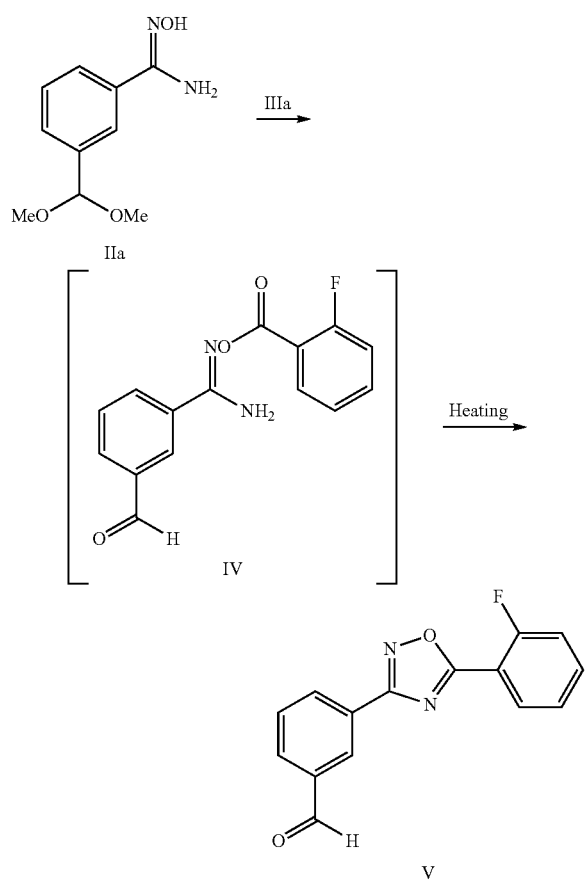

3-(dimethoxymethyl)-N'-hydroxybenzimidamide (IIa) (0.5 g, 2.38 mmol, 1.0 equiv.) and pyridine (5 mL, 10 vol) were added to a suitable reactor equipped with a stir bar and a thermometer at 20-30° C. and stirred for about 10-15 min. The reaction mixture was cooled to 0-10° C. (target 5° C.) and 2-fluorobenzoyl chloride (IIIa) (0.5 mL, 1.1 equiv.) was slowly added to the solution. Then the mixture was heated to 92-98° C. and stirred for about 20 hr. After the reaction was completed as determined by TLC analysis, the solution was cooled to ambient. The mixture was diluted with PPW (15 mL, 30 vol) and stirred at 20-30° C. for 5 min. Then the mixture was filtered and the filtered cake was washed with PPW (15 mL, 30 vol) for twice. The wet cake was suction dried at NMT 40° C. with N$_2$ purge for NLT 3 hr to give 3-[5-(2-fluorophenyl)-1,2,4-oxadiazol-3-yl]benzaldehyde (V) as pale skinny fine solid (0.52 g, 82% yield based on IIa). $^1$H-NMR (400 MHz, D$_6$-DMSO) δ10.17 (s, 1H), 8.61 (t, 1H), 8.42 (dt, 1H), 8.28 (td, 1H), 8.18 (dt, 1H), 7.84 (m, 2H), 7.57 (m, 2H).

Example 6

Synthesis of 3-[5-(2-Fluorophenyl)-1,2,4-oxadiazol-3-yl] benzoic acid (Ataluren)

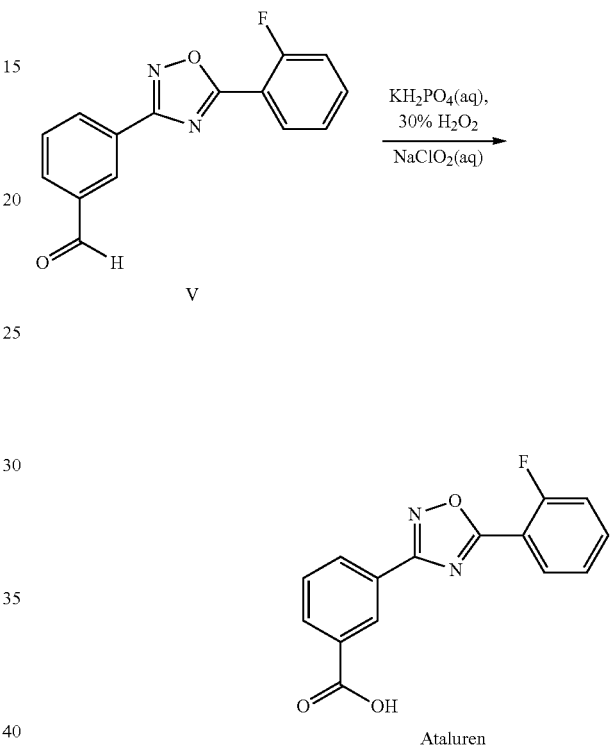

3-[5-(2-fluorophenyl)-1,2,4-oxadiazol-3-yl]benzaldehyde (V) (0.1 g, 0.373 mmol, 1.0 equiv.) and MeCN (2 mL, 20 vol) were added to a suitable reactor equipped with a stir bar and a thermometer at 20-30° C. A solution of potassium phosphate monobasic (KH$_2$PO$_4$, 0.0304 g, 0.6 equiv.) in PPW (0.5 mL, 5 vol) and 30% H$_2$O$_2$ (aq) (38 uL, 1.0 equiv.) were slowly added at this temperature. The reaction mixture was cooled to 0-10° C. (target 5° C.) and a solution of sodium chlorite (NaClO$_2$, 0.0742 g, 2.2 equiv.) in PPW (1 mL, 10 vol) was slowly added. Then the reaction mixture was warmed to 20-30° C. and stirred for 5 hr. After the reaction was completed as determined by TLC analysis, the solution was cooled to 0-10° C. A solution of sodium sulfite (Na$_2$SO$_3$, 0.037 g, 0.79 equiv.) in PPW (0.4 mL, 4 vol) was slowly added and stirred for about 5 min. 2N HCl(aq) (0.615 mL, 3.3 equiv.) was subsequently added at 0-10° C. adjusting pH to about 1. The mixture was filtered and the filtered cake was washed with PPW (0.5 mL, 5 vol) for twice. The wet cake was suction dried at NMT 40° C. with N$_2$ purge for NLT 18 hr to give 3-[5-(2-Fluorophenyl)-1,2,4-oxadiazol-3-yl] benzoic acid (Ataluren) as white solid (0.477 g, 90% yield based on V). $^1$H-NMR (400 MHz, D$_6$-DMSO) δ8.65 (s, 1H), 8.29 (m, 2H), 8.18 (m, 1H), 7.80 (m, 2H), 7.56 (m, 2H).

Example 7

Synthesis of 3-(N'-hydroxycarbamimidoyl)benzoic acid (VII)

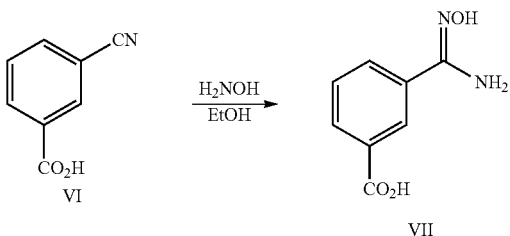

3-Cyanobenzoic acid (VI) (7.53 g, 75.2 mmol, 1.0 equiv.) and EtOH (120.5 mL, 16 vol.) were added to a suitable reactor equipped with a stir bar and a thermometer at 20-30° C. and stirred for about 5 min. A solution of potassium carbonate (21.27 g, 3.0 equiv.) in water (15 mL, 2 vol.) and hydroxylamine hydrochloric acid (10.68 g, 3.0 equiv.) were added at this temperature. Then the reaction mixture was heated to reflux and stirred for 3 hr. After the reaction was completed as determined by TLC analysis, the mixture was concentrated to near dryness under reduced pressure at NMT 85° C. to remove EtOH. After the crude product was cooled to 20-30° C., PPW (90 mL, 12 vol.) was added to dissolve the crude product. 32% HCl$_{(aq)}$ was slowly added, adjusting pH value to 3-4. This induced precipitation. The resulting slurry was filtered and the filtered cake was washed with PPW (15 mL, 2 vol.). The wet cake was suction dried at NMT 40° C. with N$_2$ purge for NLT 18 hr to give 3-(N'-hydroxycarbamimidoyl)benzoic acid (VII) as white solid (8.47 g, 91.9% yield based on VI).

Example 8

Synthesis of 3-(N'-((2-fluorobenzoyl)oxy)carbamimidoyl)benzoic acid (VIII)

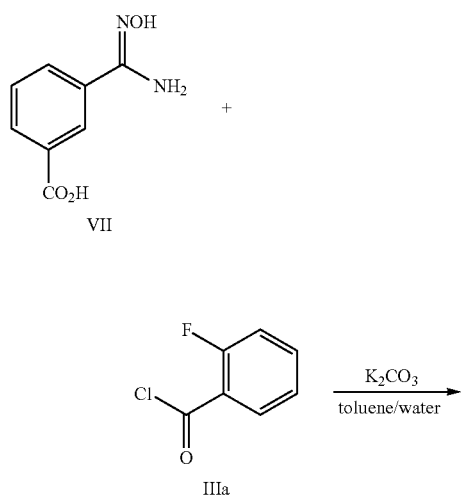

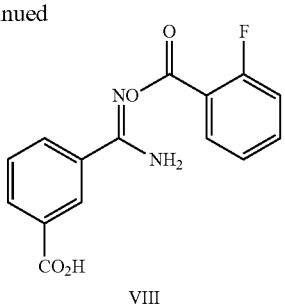

3-(N'-hydroxycarbamimidoyl)benzoic acid (VII) (2.0 g, 11.1 mmol, 1.0 equiv.) potassium carbonate (2.61 g, 18.9 mmol, 1.7 equiv.) and PPW (20 mL, 10 vol) were added to a suitable reactor equipped with a stir bar and a thermometer at 20-30° C. and stirred for about 5 min. The reaction mixture was cooled to 0-10° C. After reaching the appropriate temperature a solution of 2-Fluorobenzoyl chloride (IIIa) (2.13 g, 1.2 equiv.) in toluene (10 mL, 5 vol) was added to the reaction mixture. Then the reaction mixture was stirred at this temperature for 1 hr. After the reaction was completed as determined by TLC analysis, 2N HCl(aq) (12 mL, 2.16 equiv.) was subsequently added adjusting pH value to about 1-2 while maintaining internal temperature NMT 10° C. The mixture was filtered and the filtered cake was washed with toluene (10 mL, 5 vol). The wet cake was suction dried at NMT 40° C. with N$_2$ purge for NLT 18 hr to give 3-(N'-((2-fluorobenzoyl)oxy)carbamimidoyl)benzoic acid (VIII) as white solid (2.99 g, 89.1% yield based on VII).

Example 9

Synthesis of Ataluren

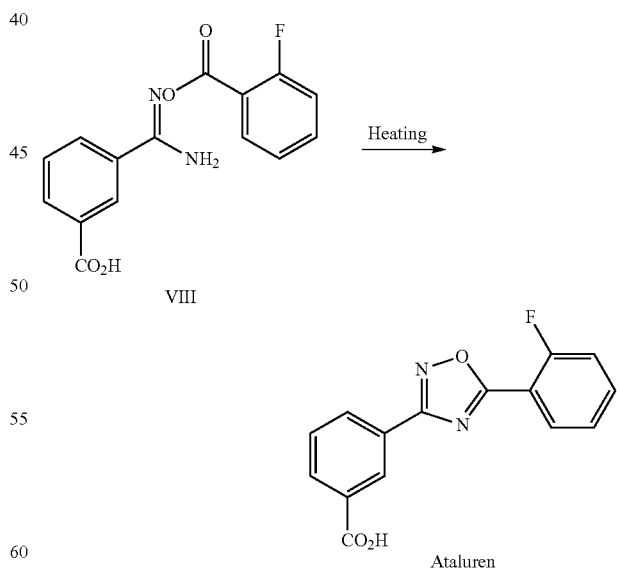

3-(N'-((2-fluorobenzoyl)oxy)carbamimidoyl)benzoic acid (VIII) (2.99 g, 9.89 mmol, 1.0 equiv.) and tert-butanol (44 mL, 14.7 vol.) were added to a suitable reactor equipped with a stir bar and a thermometer at 20-30° C. and stirred for about 5 min. The reaction mixture was heated to 80° C. and stirred for 24 hr. After the reaction was completed as determined by TLC analysis, the mixture was diluted with PPW (20 mL, 6.7 vol.). After addition of PPW, the reaction mixture was cooled to 20-30° C., forming a slurry. The slurry was filtered and the filtered cake was washed with tert-butanol (10 mL, 3.3 vol.) and PPW (10 mL, 3.3 vol.). The wet cake was suction dried at NMT 40° C. with $N_2$ purge for NLT 18 hr to give 3-[5-(2-Fluorophenyl)-1,2,4-oxadiazol-3-yl] benzoic acid (Ataluren) as white solid (2.48 g, 88.4% yield based on VIII).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for the preparation of ataluren

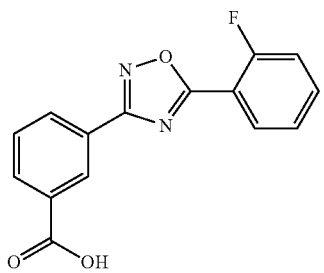 [SMILES: O=C(O)c1cccc(-c2noc(-c3ccccc3F)n2)c1]

the process comprising:
a) contacting a compound of formula I

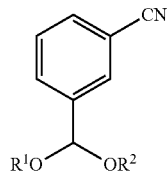

with hydroxylamine to provide a compound of formula II

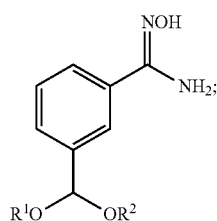

and
b) converting the compound of formula II to provide ataluren;

wherein:
$R^1$ and $R^2$ are independently selected from the group consisting of $C_1$-$C_6$ alkyl and $C_1$-$C_6$ acyl; or
$R^1$ and $R^2$ are taken together to form an optionally substituted 5-7 member cyclic acetal.

2. The process of claim 1, wherein step b) further comprises: i) contacting the compound of formula II with a compound of formula III

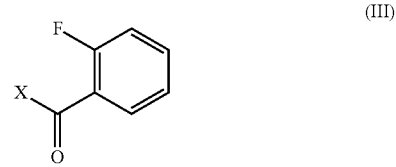

to provide a compound of formula IV

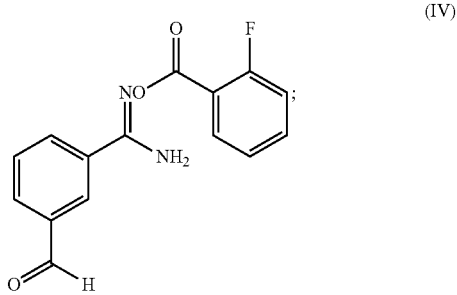

ii) converting the compound of formula IV to provide a compound of formula V

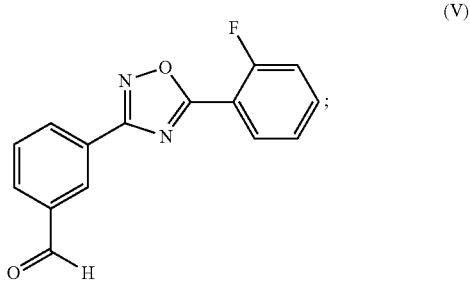 [SMILES: O=Cc1cccc(-c2noc(-c3ccccc3F)n2)c1]

and
iii) oxidizing the compound of formula V to ataluren;
wherein X is a leaving group.

3. The process of claim 2, wherein step i) is carried out in a two-phase solvent system having a basic aqueous solution and an organic solvent.

4. The process of claim 3, wherein the basic aqueous solution is selected from the group consisting of aqueous $NaHCO_3$, aqueous $Na_2CO_3$, aqueous $K_2CO_3$ and mixtures thereof.

5. The process of claim 4, wherein the basic aqueous solution is aqueous $NaHCO_3$.

6. The process of claim 3, wherein the organic solvent is selected from the group consisting of ethyl acetate, toluene, dichloromethane (DCM), 2-methyltetrahydrofuran (2-MeTHF) and mixtures thereof.

7. The process of claim 6, wherein the organic solvent is ethyl acetate.

8. The process of claim 2, wherein steps i) to ii) are conducted in a one-pot reaction.

9. The process of claim 8, wherein steps i) to ii) are conducted in an organic solvent selected from the group consisting of pyridine, toluene, xylene and mixtures thereof.

10. The process of claim 9, wherein the organic solvent is pyridine.

11. The process of claim 8, wherein steps i) to ii) are conducted in an organic base selected from the group consisting of pyridine, triethylamine (TEA), diisopropylethylamine (DIPEA) and mixtures thereof.

12. The process of claim 8, wherein step ii) is conducted in an internal temperature of 92-98° C.

13. The process of claim 2, wherein X is selected from the group consisting of a halogen, an O-succinimide, an —O—$R^a$, a carboxylate, a phenoxide, and an anhydride; wherein $R^a$ is $C_1$-$C_6$ alkyl.

14. The process of claim 13, wherein X is a halogen.

15. The process of claim 2, wherein step iii) is carried out using an oxidant selected from the group consisting of a chlorite, a transition metal catalyst, nickel peroxide, meta-chloroperoxybenzoic acid (m-CPBA), tert-butyl hydroperoxide (TBHP), potassium peroxomonosulfate (Oxone), and mixtures thereof.

16. The process of claim 15, wherein the oxidant is a chlorite selected from the group consisting of chlorous acid, magnesium chlorite, sodium chlorite, and potassium chlorite.

17. The process of claim 16, wherein the oxidant is sodium chlorite.

18. The process of claim 16, wherein the chlorite is buffered with an electrolyte selected from the group consisting of HCl/sodium citrate, citric acid/sodium citrate, acetic acid/sodium citrate, potassium dihydrogen phosphate, dipotassium phosphate/sodium dihydrogen phosphate, and disodium phosphate mixtures.

19. The process of claim 18, where the electrolyte is potassium dihydrogen phosphate.

20. The process of claim 1, wherein the compound of formula I is prepared by contacting 3-cyanobenzaldehyde with an aldehyde protecting reagent.

21. The process of claim 20, wherein the aldehyde protecting reagent is selected from the group consisting of trimethyl orthoformate (TMOF), triethyl orthoformate, triethyl orthoacetate, trimethyl orthoacetate, acetic anhydride, ethylene glycol, and propylene glycol.

22. The process of claim 21, wherein the aldehyde protecting reagent is trimethyl orthoformate (TMOF).

23. The process of claim 1, wherein the compound of formula I is a compound of formula Ia

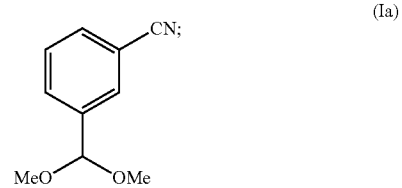 [SMILES: COC(OC)c1cccc(C#N)c1]

and the compound of formula II is a compound of formula IIa

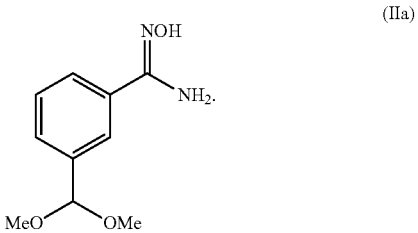

24. The process of claim 2, wherein the compound of formula III is a compound of formula IIIa

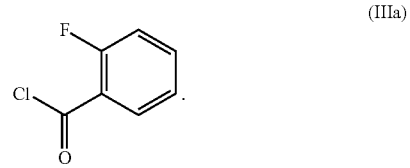

* * * * *